United States Patent [19]

Kinishi et al.

[11] Patent Number: 5,284,978

[45] Date of Patent: Feb. 8, 1994

[54] METHOD FOR PRODUCING DIPHENYL SULFONE COMPOUNDS

[75] Inventors: Ryoichi Kinishi, Fukuoka; Yoshihiro Ozaki, Suzuka, both of Japan

[73] Assignee: Yoshitomi Pharmaceutical Industries, Ltd., Osaka, Japan

[21] Appl. No.: 35,486

[22] Filed: Mar. 22, 1993

Related U.S. Application Data

[63] Continuation of Ser. No. 761,915, filed as PCT/JP91/00090, Jan. 29, 1990, abandoned.

[30] Foreign Application Priority Data

Jan. 29, 1990 [JP] Japan .................................. 2-19685

[51] Int. Cl.⁵ .......................................... C07C 315/04
[52] U.S. Cl. .......................................... 568/33
[58] Field of Search .......................................... 568/33

[56] References Cited

U.S. PATENT DOCUMENTS 4,568,766  2/1986  Yahagi et al. .......................... 568/33

FOREIGN PATENT DOCUMENTS

| 466096 | 1/1992 | European Pat. Off. | ............ 568/33 |
| 59-225157 | 12/1984 | Japan . | |
| 60-056949 | 2/1985 | Japan . | |

Primary Examiner—Marianne M. Cintins
Assistant Examiner—Margaret J. Page
Attorney, Agent, or Firm—Wenderoth, Lind & Ponack

[57] ABSTRACT

A method of producing diphenyl sulfone compounds of the formula (I)

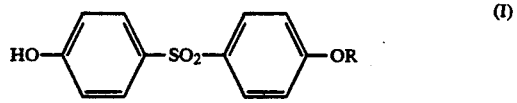

wherein R is an alkyl having 1 to 8 carbon atoms, a cycloalkyl having 3 to 8 carbon atoms, an alkenyl having 2 to 8 carbon atoms or an arylalkyl which may have substituent(s) on the aromatic ring, comprising reacting 4,4'-dihydroxydiphenyl sulfone with a compound of the formula

R—X wherein R is as defined above and X is halogen, characterized by conducting the reaction in 0.3–1.5 weight parts of an aqueous solvent per weight part of 4,4'-dihydroxydiphenyl sulfone in the presence of 1.5–3 moles of an alkali per mole of 4,4'-dihydroxydiphenyl sulfone. Since the method of the invention permits production of 4-substituted hydroxy-4'-hydroxydiphenyl sulfones, specifically 4-n-propoxy-4'-hydroxydiphenyl sulfone or 4-isopropoxy-4'-hydroxydiphenyl sulfone using an inexpensive solvent, with good selectivity and economical feasibility, they are industrially advantageous.

3 Claims, No Drawings

METHOD FOR PRODUCING DIPHENYL SULFONE COMPOUNDS

This application is a continuation of application Ser. No. 07/761,915 filed as PCT/JP91/00090, Jan. 29, 1991, now abandoned.

TECHNICAL FIELD

The present invention relates to a novel method for producing diphenyl sulfone compounds, namely, 4-substituted hydroxy-4'-hydroxydiphenyl sulfones of the formula (I)

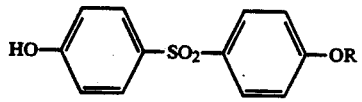

wherein R is as defined below, which are useful as color developers in thermosensitive recording materials.

BACKGROUND ART

International Publication No. WO84/02882 discloses that among the compounds of formula (I), the compound wherein R is an alkyl having 2 to 5 carbon atoms, benzyl or phenethyl is useful as a developer for thermosensitive recording papers. Further, Japanese Patent Publication No. 61198/1988 discloses thermosensitive recording papers containing a compound of formula (I) wherein R is an alkyl having 6 to 20 carbon atoms.

These diphenyl sulfone developer compounds give improved coloring sensitivity, shelf life and light resistance in comparison with conventional phenol developers, and have recently been employed not only for recording papers for information, communication recording devices such as facsimile, etc. but also for thermosensitive bar cord labels for POS (Point of Sales) information management systems, various tickets, and the like.

As regards the methods of producing 4-substituted hydroxy-4'-hydroxydiphenyl sulfones which are monoether derivatives of 4,4'-dihydroxydiphenyl sulfone (hereinafter sometimes referred to as bisphenol S), methods which comprise reacting bisphenol S with a halide such as an alkyl halide or aralkyl halide in the presence of an alkali in a polar solvent such as dimethylformamide or alcohol are disclosed in Japanese Patent Unexamined Publication Nos. 20493/1983, 82788/1983, 13852/1985 and 56949/1985. These methods include the use of a polar solvent which dissolves the reactants and reaction products well, and are advantageous in that the charge weight per unit volume of reactor can be increased. However, the use of such solvent or dimethylsulfoxide gives rise to a difficulty in improving reaction selectivity, and also a diether derivative, i.e. 4,4'-di-substituted hydroxydiphenyl sulfone is formed in a non-negligible amount as a by-product. In addition, dimethylformamide, dimethylsulfoxide, etc. are relatively expensive so that recovery and recirculation steps need to be added.

Japanese Patent Unexamined Publication No. 255259/1988 proposes a method wherein a monoether derivative, i.e. 4-alkoxy-4'-hydroxydiphenyl sulfone, is produced by condensing an alkoxybenzenesulfonyl chloride and diphenyl carbonate in the presence of a Lewis acid, followed by hydrolysis of the carbonate bond. While this method solves the selectivity problem, it also poses various problems upon industrial application, such as lengthy processes, need to use phosgene which is highly toxic for the production of diphenyl carbonate, or the like.

Furthermore, Japanese Patent Unexamined Publication No. 225157/1982 discloses a method wherein a monobenzyl ether, i.e. 4-benzyloxy-4'-hydroxydiphenyl sulfone, is produced by dissolving 4,4'-dihydroxydiphenyl sulfone (1 mole) in water containing 0.8-1.2 equivalent of a hydroxide and/or a salt of alkali metal and/or alkaline earth metal, and reacting the same with 0.8-1.2 equivalent of benzyl chloride at 40°-80° C., followed by separation of resulting 4-hydroxy-4'-benzyloxydiphenyl sulfone. In this method, a monosodium salt is produced since the amount of the alkali relative to bisphenol S is 0.8-1.2 equivalent amount, but the monosodium salt has small solubility in water, necessitating increased amount of water which leads to low volume efficiency of the reactor and low reaction speed.

The object of the invention is to provide a method of producing 4-substituted hydroxy-4'-hydroxydiphenyl sulfones, having good selectivity and economical feasibility by simpler reaction steps, which shall overcome the problems as described.

DISCLOSURE OF THE INVENTION

The present inventors have conducted intensive studies on methods of producing monoether derivatives of bisphenol S, namely, 4-substituted hydroxy-4'-hydroxydiphenyl sulfones from bisphenol S and alkyl halide, aralkyl halide, etc., and found that the objective monoether derivatives can be produced with good selectivity and economical feasibility under particular conditions, which resulted in completion of the invention. Thus, the present invention provides a method of producing diphenyl sulfone compounds of the formula (I)

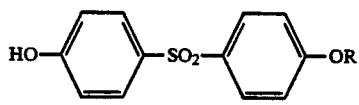

wherein R is an alkyl having 1 tq 8 carbon atoms, a cycloalkyl having 3 to 8 carbon atoms, an alkenyl having 2 to 8 carbon atoms or an arylalkyl which may have a substituent(s) on the aromatic ring, by reacting 4,4'-dihydroxydiphenyl sulfone and a compound of the formula (II)

R—X (II)

wherein R is as defined above and X is halogen, characterized by conducting the reaction in 0.3-1.5 weight parts of an aqueous solvent per weight part of 4,4'-dihydroxydiphenyl sulfone in the presence of 1.5-3 moles of an alkali per mole of 4,4'-dihydroxydiphenyl sulfone.

As the compounds of formula (II) which are used in the method of the invention, there may be mentioned alkyl halides such as methyl halide, ethyl halide, n-propyl halide, isopropyl halide, butyl halide, pentyl halide, hexyl halide, heptyl halide, octyl halide, etc., alkenyl halides such as allyl halide, etc., cycloalkyl halides such as cyclohexyl halide, methylcyclohexyl halide, etc., benzyl halides or phenethyl halides which may have 1 to 3 substituents selected from halogen (e.g. chlorine, bromine, etc.), an alkyl having 1 to 4 carbon atoms, an alkoxy having 1 to 4 carbon atoms (e.g. methoxy, ethoxy, propoxy, isopropoxy, butoxy, etc.), hydroxy, a haloalkyl having 1 to 4 carbon atoms (e.g. trifluoromethyl, trifluoroethyl, etc.), nitro and amino, on the aromatic ring, and the like. Specifically, bromides and iodides are preferable among halides. According to the method of the present invention, excessive use of the compounds of formula (II) does not cause a drastic fall in reaction selectivity.

As the alkali used as a trapping agent for hydrogen halide which is produced along with the progress of the reaction, preferred are alkali metal hydroxides such as sodium hydroxide, potassium hydroxide, etc. and alkali metal carbonates such as sodium carbonate, potassium carbonate, etc., with preference given to alkali metal hydroxides.

The amount of the alkali combined with the amount of water exerts great influence on reaction selectivity. That is, the amount of the alkali is preferably 1.5-3 moles per mole of bisphenol S and the amount of water is preferably 0.3-1.5 weight parts per weight part of bisphenol S. In case where the amount of the alkali is below 1.5 moles per mole of bisphenol S, the reaction selectivity is poor, and where it is beyond 3 moles, it decomposes compounds of formula (II). Further, when the amount of water is below 0.3 weight part per weight part of bisphenol S, stirring becomes unconductible, and when it is beyond 1.5 weight parts, the reaction efficiency becomes poor.

The aqueous solvent preferably contains metal salts represented by the formula (III)

$$M_mY_n \quad \quad \quad (III)$$

wherein M is an alkali metal or an alkaline earth metal, Y is halogen, carbonate ion, hydrogencarbonate ion, sulfate ion or phosphate ion, and m and n are respectively 1 or 2. As such metal salts, use can be made of metal halides such as sodium chloride, sodium bromide, sodium iodide, potassium chloride, potassium bromide, potassium iodide, calcium chloride, etc., alkali metal sulfates such as sodium sulfate, potassium sulfate, etc., alkali metal phosphates such as sodium phosphate, potassium phosphate, etc., alkali metal carbonates such as sodium carbonate, potassium carbonate, and hydrogencarbonates such as sodium hydrogencarbonate, potassium hydrogencarbonate, etc., with preference given to metal halides. Addition of metal salts is unnecessary when the amount of water is small. When a metal salt is to be added, the reaction selectivity can be enhanced when it is added in an amount of up to 1 weight part per weight part of bisphenol S. Even when a metal halide of formula (III) to be added to water is the same kind of metal halide produced stoichiometrically by said reaction, the metal salt is to be added independently in the present invention. The metal salts to be used may be added to water in advance before the initiation of the reaction or after the initiation thereof.

The reaction is conducted by adding bisphenol S, an alkali, and if necessary, a metal salt, to water for dissolution and pouring or dropwise adding an etherification agent such as an alkyl halide, and the like. The reaction proceeds at a temperature between room temperature and 150° C. for 6-24 hours under normal pressure or under pressurization, preferably at a temperature between 50° C. and 120° C. for 6-15 hours. The objective product with high purity can be obtained by a conventional means such as solvent extraction, washing, recrystallization, etc. following the reaction.

Hereunder follow working examples and comparative examples to further illustrate the present invention, to which the invention is by no means limited.

EXAMPLE 1

Sodium hydroxide (8 g) and water (25 g) were charged in a glass flask equipped with a thermometer, a stirrer rod and a condenser, and after dissolution, 4,4'-dihydroxydiphenyl sulfone (25 g) was added thereto and dissolved by heating. The temperature of the solution was raised to 70° C., and n-propyl bromide (12.3 g) was added dropwise with stirring over 1 hour, followed by stirring at 65°-72° C. for 12 hours. HPLC analysis of the reaction product showed the following composition: 4,4'-dihydroxydiphenyl sulfone: 25%, 4-n-propoxy-4'-hydroxydiphenyl sulfone: 68% and 4,4'-di-n-propoxydiphenyl sulfone: 7%. To the reaction mixture was added toluene, and the diether compound was removed by extraction into the toluene layer. Thereafter, ethyl acetate was added to the water layer for extracting the objective compound into the ethyl acetate layer. The unreacted 4,4'-dihydroxydiphenyl sulfone remained in the water layer. The ethyl acetate layer was neutralized with diluted hydrochloric acid and washed with water, after which the residue obtained by evaporating the solvent was recrystallized from toluene to give 19 g of 4-n-propoxy-4'-hydroxydiphenol sulfone as white crystals, m.p. 152°-154° C.

EXAMPLE 2

Sodium hydroxide (8 g), sodium bromide (5.1 g), water (30 g) and 4,4'-dihydroxydiphenol sulfone (25 g) were charged in a flask. After dissolution, n-propyl bromide (12.3 g) was dropwise added at 70° C. over 1 hour. The reaction was conducted in the same manner as in Example 1. The composition of the reaction product by HPLC area % was 4,4'-dihydroxydiphenyl sulfone: 18%, 4-n-propoxy-4'-hydroxydiphenyl sulfone: 80% and 4,4'-di-n-propoxydiphenyl sulfone: 2%.

EXAMPLE 3

The same procedure as in Example 1 was repeated except that sodium hydroxide was used in an amount of 12 g and water was used in an amount of 16 g. The composition of the reaction product was 4,4'-dihydroxydiphenyl sulfone: 22%, 4-n-propoxy-4'-hydroxydiphenyl sulfone: 74% and 4,4'-di-n-propoxy-diphenylsulfone: 4%.

EXAMPLE 4

The same procedure as in Example 2 was repeated except that isopropyl bromide (12.3 g) was used in place of n-propyl bromide. The composition of the reaction product was 4,4'-dihydroxydiphenyl sulfone: 20%, 4-isopropoxy-4'-hydroxydiphenyl sulfone: 78% and 4,4'-di-isopropoxydiphenyl sulfone: 2%. Subsequently, the same procedure as in Example 1 was followed to give 21.5 g of 4-isopropoxy-4'-hydroxydiphenyl sulfone as white crystals, m.p. 128°-129° C.

EXAMPLE 5

The same procedure as in Example 2 was repeated except that sodium chloride (5.8 g) was used in place of sodium bromide and benzyl chloride (12.7 g) was used in place of n-propyl bromide. The composition of the reaction product was 4,4'-dihydroxydiphenyl sulfone: 15%, 4-benzyloxy-4'-hydroxydiphenyl sulfone: 83% and 4,4'-di-benzyloxydiphenyl sulfone: 2%. Subsequently, the same procedure as in Example 1 was followed to give 26 g of 4-benzyloxy-4'-hydroxydiphenyl sulfone as white crystals, m.p. 168° C.

EXAMPLE 6

The same procedure as in Example 1 was repeated except that allyl chloride (7.65 g) was used in place of n-propyl bromide. The composition of the reaction product was 4,4'-dihydroxydiphenyl sulfone: 20% and 4-allyloxy-4'-hydroxydiphenyl sulfone: 74%. By the same procedure as in Example 1, there was obtained 4-allyloxy-4'-hydroxydiphenyl sulfone as white crystals, m.p. 168°-172° C.

COMPARATIVE EXAMPLE 1

4,4'-Dihydroxydiphenyl sulfone (25 g), dimethylformamide (150 g) and sodium hydroxide (4 g) were charged and the temperature of the solution was adjusted to 60° C. n-Propyl bromide (12.3 g) was dropwise added, and the reaction was carried out at 60°-70° C. for 4 hours. The composition of the reaction product was 4,4'-dihydroxydiphenyl sulfone: 27%, 4-n-propoxy-4'-hydroxydiphenyl sulfone: 46% and 4,4'-di-n-propoxydiphenyl sulfone: 26%.

COMPARATIVE EXAMPLE 2

4,4'-Dihydroxydiphenyl sulfone (25 g), sodium hydroxide (4 g) and water (30 g) were charged in a flask, and the mixture was heated. The content did not dissolve completely but became slurry. To this slurry was added n-propyl bromide (12.3 g), and the reaction was carried out at 65°-72° C. for 12 hours. The composition of the reaction product was 4,4'-dihydroxydiphenyl sulfone: 90%, 4-n-propoxy-4'-hydroxydiphenyl sulfone: 10% and 4,4'-di-n-propoxydiphenyl sulfone: trace amount.

COMPARATIVE EXAMPLE 3

The same procedure as in Example 1 was repeated except that 4,4'-dihydroxydiphenyl sulfone (25 g), sodium hydroxide (8 g) and water (50 g) were used. The composition of the reaction product was 4,4'-dihydroxydiphenyl sulfone: 32%, 4-n-propoxy-4'-hydroxydiphenyl sulfone: 39% and 4,4'-di-n-propoxydiphenyl sulfone: 29%.

COMPARATIVE EXAMPLE 4

Sodium hydroxide (20 g), water (800 g) and 4,4'-dihydroxydiphenyl sulfone (125 g) were charged in a 1 l-flask for dissolution. The temperature of the solution was retained at 55°-56° C., and isopropyl bromide (62 g) was added thereto, followed by stirring for 24 hours. The reaction mixture was analyzed by HPLC and the area % was 4,4'-dihydroxydiphenyl sulfone: 57.8%, 4-isopropoxy-4'-hydroxy-diphenyl sulfone: 39.8% and 4,4'-diisopropoxydiphenyl sulfone: 1.6%.

It is evident from the above-mentioned working examples and comparative examples that according to the method of the invention, 4-substituted hydroxy-4'-hydroxydiphenyl sulfones, specifically 4-n-propoxy-4'-hydroxydiphenyl sulfone or 4-isopropoxy-4'-hydroxydiphenyl sulfone, can be produced using an inexpensive solvent, with good selectivity and economical feasibility.

While the present invention has been described by the foregoing specification including working examples and so on, the embodiments described herein, in particular, can be changed and modified in various manners within the scope and the spirit of the present invention.

What is claimed is:

1. A method of producing a diphenyl sulfone compound of the formula (I)

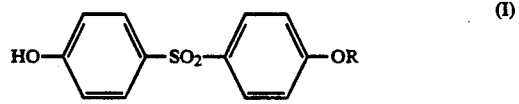

wherein R is an alkyl having 1 to 8 carbon atoms, comprising:
 reacting 4,4'-dihydroxydiphenyl sulfone with 2-3.0 moles of alkali metal hydroxide per mole of the 4,4'-dihydroxydiphenyl sulfone in 0.3-1.5 parts by weight of an aqueous solvent per part by weight of the 4,4'-dihydroxydiphenyl sulfone, to obtain 4,4'-dihydroxydiphenyl sulfone dialkali metal salt; and
 reacting the 4,4'-dihydroxydiphenyl sulfone dialkali metal salt with a compound of the formula (II)

R—X      (II)

wherein R is as defined above and X is a halogen atom.

2. A method according to claim 1, wherein the aqueous solvent contains, in addition to an alkali metal halide produced in the reaction system, up to 1 part by weight of alkali metal halide per part by weight of the 4,4'-dihydroxydiphenyl sulfone.

3. A method according to claim 1, wherein the compound of the formula (I) is 4-n-propoxy-4'-hydroxydiphenyl sulfone, 4-isopropoxy-4'-hydroxydiphenyl sulfone, or 4-n-butoxy-4'-hydroxydiphenyl sulfone.

* * * * *